United States Patent [19]

Swim et al.

[11] Plant 5,219

[45] Apr. 17, 1984

[54] ROSE PLANT CV. AROART

[75] Inventors: Herbert C. Swim; Jack E. Christensen, both of Ontario, Calif.

[73] Assignee: Armstrong Nurseries, Inc., Ontario, Calif.

[21] Appl. No.: 413,454

[22] Filed: Aug. 31, 1982

[51] Int. Cl.[3] ..... A01H 5/00

[52] U.S. Cl. ..... Plt./21

[58] Field of Search ..... Plt./20, 21

*Primary Examiner*—James R. Feyrer

*Attorney, Agent, or Firm*—Synnestvedt & Lechner

[57] ABSTRACT

A new variety of rose plant of the hybrid tea class, being a tall, bushy, half-hardy outdoor seedling, particularly adapted for garden decoration. This new rose cultivar is unique and distinguishable from existing rose cultivars by the following combination of characteristics: its extremely large foliage attractively clothes the plant, covering unsightly stems; the inside of each petal is very velvety, lending an effect of iridescence to the red coloration; the deep red coloration is relatively uniform throughout the life of the flower; its flowers are very slow opening both on the plant and in the vase; and its abundant production of strong, long-stemmed flowers well lend the variety for cutting.

1 Drawing Figure

This invention relates to a new class of hybrid tea rose. The plant is a seedling of the half-hardy, tall bushy outdoor type, cultivated for garden decoration. It was first propagated in Ontario, Calif. References to the growth and behavior of the plant pertain to plants raised in Southern California.

This new rose cultivar is unique and distinguishable from existing rose cultivars by the following combination of characteristics: its extremely large foliage attractively clothes the plant, covering unsightly stems; the inside of each petal is very velvety, lending an effect of iridescence to the red coloration; the deep red coloration is relatively uniform throughout the life of the flower; its flowers are very slow opening both on the plant and in the vase; and its abundant production of strong, long-stemmed flowers well lend the variety for cutting.

The new variety was propagated by Herbert C. Swim and Jack E. Christensen in Ontario, Calif., having as its seed parent "Pink Parfait" (U.S. Plant Pat. No. 1,904) and, as its pollen parent, "Yuletide" (U.S. Plant Pat. No. 1,391). It holds its distinguishing characteristics through succeeding propagations by budding.

The new variety usually bears its flowers singly, but sometimes two to three blooms are carried on one stem, in irregular flat clusters. The stems are strong and long. The plant blooms abundantly outdoors, and nearly continuously during the growing season. It has a slight tea fragrance.

This new rose cultivar may be distinguished from its seed parent, Pink Parfait, by the following combination of characteristics.

Whereas Pink Parfait bears flowers of a predominate pink coloration, the new cultivar bears flowers of a predominate red coloration essentially as described and illustrated herein.

The new rose bears flowers with 35 to 45 petals, whereas Pink Parfait bears flowers of significantly lower petalage (20 to 25).

Whereas the new cultivar is classified as a hybrid tea, Pink Parfait is classified as a hybrid grandiflora.

Pink Parfait bears flowers with numerous pistils (about 110), whereas the new rose bears flowers with significantly fewer pistils (about 70).

This new rose cultivar may be distinguished from its pollen parent, Yuletide, by the following combination of characteristics.

Whereas Yuletide bears flowers of a light red coloration, the new cultivar bears flowers of a significantly deeper red coloration essentially as described and illustrated herein.

The foliage of Yuletide is average in size, whereas the foliage of the new rose is significantly larger.

Whereas the new rose cultivar is intended specifically for use as garden decoration, Yuletide is used only as a greenhouse rose.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the R.H.S. Colour Chart published by The Royal Horticultural Society of London, England.

BUD

The peduncle is short to average in length and average in caliper, being erect, stiff and moderately smooth, with some stipitate glands.

Before the calyx breaks, the bud is medium in size, medium-length, pointed and ovoid in form and with some foliaceous appendages and a few stipitate glands on the surface of the bud. Usually, slender foliaceous parts extend beyond the tip of the bud equal to from one-fourth to one-half of its length.

As the calyx breaks, the color is between Red, 53A and Red Purple, 59A. The inner surface of the sepals carries a fine, wooly tomentum. Margins of the sepals are lined with stipitate glands and hairs.

As the first petal opens, the bud is of average size, of medium length, pointed and ovoid in form. The color on the outside of the petal is between Red Purple, 60A and Red, 46A and sometimes blended with between Black, 202A and Greyed-Purple, 183A and with a very small basal attachment point near Yellow, 2D. The inside surface of the petal has a basal attachment point of near Yellow, 2D and suffuses to between Red, 53A and Red, 46A. The bud opens up well, and is not prevented from opening by cold, hot, wet or dry weather.

BLOOM

The size of the bloom when fully open is of average size, ranging from 3½ to 4½ inches. The petalage is double, with from 35 to 45 petals, plus from 1 to 5 petaloids arranged regularly. The bloom is full and high centered at first, becoming open to cupped. At first the petals remain somewhat cupped, with tips reflexed outward, and later at maturity becoming less tightly cupped, with tips reflexed outward.

The petals are of a thick texture; very velvety on the inside and shiny to satiny on the outside. The outside petals are broadly obovate with a rounded apex; the intermediate petals are round to broadly obovate and with a rounded apex. The inside petals are obovate and sometimes have a notched apex. The colors may be modified by being blotched, shaded and/or washed or tinted with other colors.

The description immediately following is of a newly opened flower of a plant grown outdoors in the month of July in Ontario, Calif.

The outer surface of outside, intermediate and inside petal has a small basal attachment point that is near Yellow, 2D which suffuses to between Red-Purple, 60A and Red, 47A. The inner surface of all petals has a basal attachment point that is near Yellow, 2D and suffuses to between Red, 53A and Red, 46A. The outer edges of the inside surface of the outside petal sometimes darkens to between Black, 202A and Greyed-Purple, 187A; the intermediate petals show less darkening and the inner petals show no darkening on the edges of the inside surface.

The description which follows was made from a rose that was open for three days. It had been grown outdoors in the month of July, at Ontario, Calif.

The outer surface of the outside and inside petals has a small basal attachment point near Yellow, 4D which suffuses to between Red-Purple, 60C and 60B. The inner surface of the outside and inside petals has a basal attachment point near Yellow, 4D that suffuses to between Red, 53C and Red, 47A; areas exposed to sunlight sometimes darken to between Red-Purple, 59A and Red, 46A.

The general color effect of the newly opened flower is between Red, 53A and Red, 46A. The bloom after being three days open, gives a general color effect between Red, 53C and Red, 46A. The petals drop off cleanly. They are not particularly affected by cold, hot, wet or dry weather.

The flower on the bush in the garden persists from three to four days in the month of July. Cut roses grown outdoors and kept at living-room temperatures will last from four to five days in the month of July.

REPRODUCTIVE ORGANS

There is an average number to many stamens which are arranged regularly about the pistils.

Filaments are of medium length and most are with anthers.

The anthers are of medium size to large, all opening approximately at once. When immature, the color is near Yellow-Orange, 17B, and when mature, the color is near Greyed-Orange, 165A.

Pollen is moderate and near Yellow-Orange, 17D in color.

There are an average number (approximately 70) of pistils.

The styles are very uneven, of short to average length, thin caliper, and loosely bunched.

The stigma is near Yellow, 11A.

The ovaries are all enclosed in the calyx.

This variety does not normally set hips under Ontario, Calif. growing conditions.

FOLIAGE

The compound leaves comprise from three to five leaflets. They occur abundantly, are of a very large size, moderately heavy and semi-glossy. The leaflets are oval in shape, have an acute apex and an acute base. The margin is simply serrate.

The upper surface of the mature foliage is between Yellow-Green, 147A and Green, 137A. The under surface is a color between Green, 138B and Yellow-Green, 148C.

The young foliage has an upper surface which is between Greyed-Purple, 183A and Greyed-Purple, 185A in color. The under surface is between Greyed-Purple, 187B and Greyed-Purple, 183A.

The rachis is average in size, the upper side being grooved and with some stipitate glands on the edges. The underside is sparsely prickly and with some stipitate glands.

The stipules are medium-length to long, moderately narrow, with medium-length points turning out at an angle of more than 45°.

The plant displays a more than average resistance to mildew and blackspot when compared to other varieties grown under comparable conditions in the same locality.

GROWTH

The plant is of bushy, upright habit, and much branched. It displays a vigorous growth. The canes are medium to heavy in caliper.

The main stems are near Yellow-Green, 152A, in color. They bear several large prickles which are of short to medium-length, almost straight, with a medium-length broad base. The color is near Greyed-Orange, 166D. There are very few small prickles near Greyed-Orange, 166D, in color and no hairs.

The branches are between Yellow-Green, 146A and Yellow-Green, 147A in color. They bear several large prickles which are of short to medium length, almost straight, and with a medium-length broad base. The color is near Greyed-Orange, 166B. There are a few small prickles near Greyed-Orange, 166B in color, and no hairs.

New shoots have a color between Green, 144A and Yellow-Green, 146A and are sometimes blushed with near Greyed-Purple, 183A. There are several large prickles which are moderately short, almost straight and with a medium length broad base. The color is near Greyed-Purple, 183B. There are several small prickles and a few hairs (both near Greyed-Purple, 183B, in color).

We claim:

1. A new and distinct variety of rose plant of the hybrid tea class, substantially as herein shown and described, being particularly characterized in its extremely large foliage; its very velvety texture on the inside of each petal; its uniform red coloration throughout the flower life; its slow opening; and its abundant production of long-stemmed flowers.

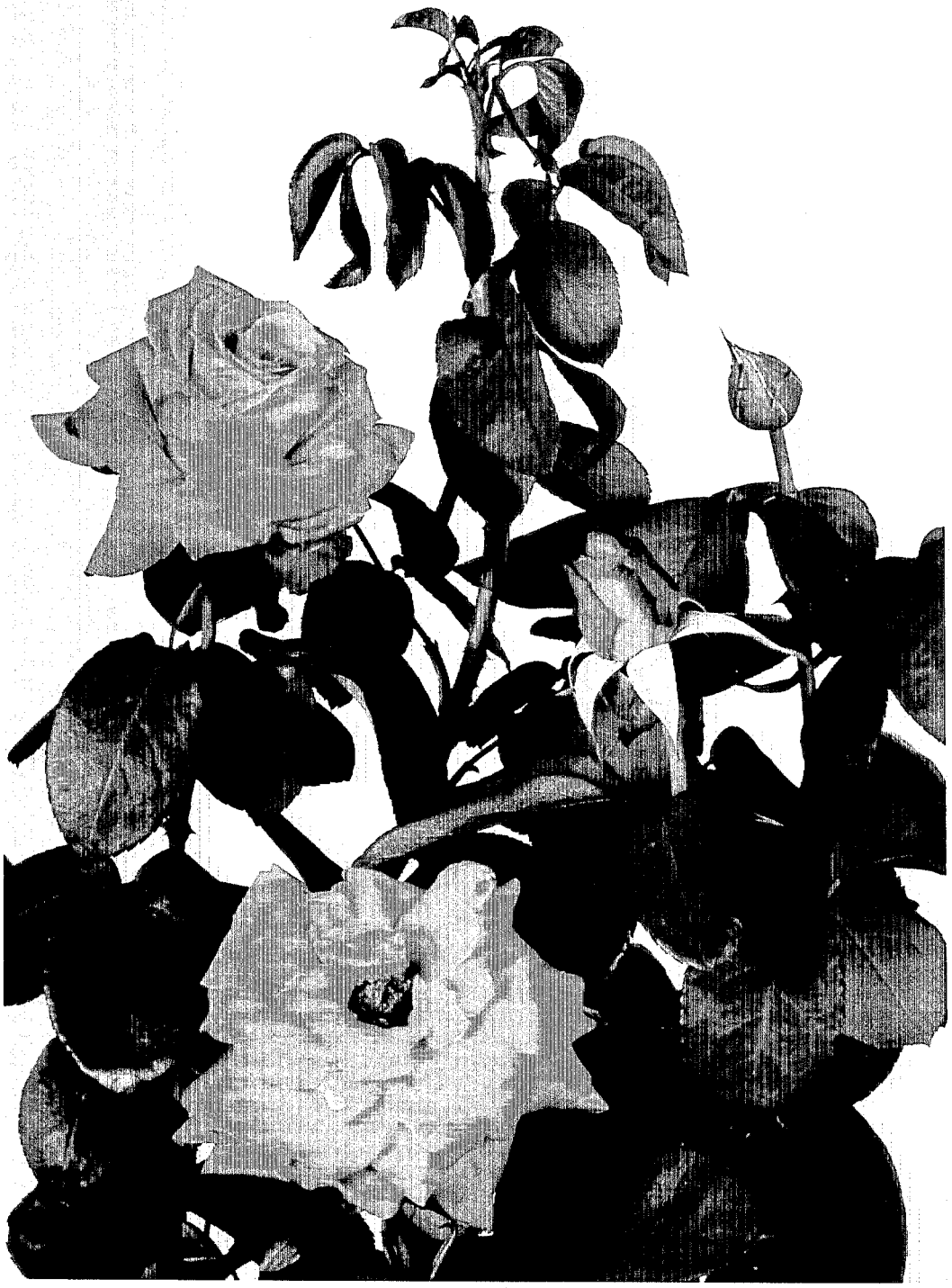

* * * * *